US008309710B2

(12) United States Patent
Sierzchala et al.

(10) Patent No.: US 8,309,710 B2
(45) Date of Patent: *Nov. 13, 2012

(54) USE OF N-ALKYL IMIDAZOLE FOR SULFURIZATION OF OLIGONUCLEOTIDES WITH AN ACETYL DISULFIDE

(75) Inventors: Agnieszka B. Sierzchala, Boulder, CO (US); Douglas J Dellinger, Boulder, CO (US); Paul A. Metz, Loveland, CO (US); Victor R Mokler, Golden, CO (US)

(73) Assignee: Agilent Technologies, Inc., Santa Clara, CA (US)

( * ) Notice: Subject to any disclaimer, the term of this patent is extended or adjusted under 35 U.S.C. 154(b) by 471 days.

This patent is subject to a terminal disclaimer.

(21) Appl. No.: 12/494,118

(22) Filed: Jun. 29, 2009

(65) Prior Publication Data

US 2010/0331532 A1    Dec. 30, 2010

(51) Int. Cl.
*C07H 1/00* (2006.01)
*C07H 21/00* (2006.01)
*C07D 233/58* (2006.01)
*C07C 321/12* (2006.01)

(52) U.S. Cl. ... 536/124; 536/26.5; 536/25.3; 548/335.1; 568/22; 568/25

(58) Field of Classification Search ............... 536/124, 536/26.5, 25.3; 548/335.1; 568/22, 25
See application file for complete search history.

(56) References Cited

U.S. PATENT DOCUMENTS

| 4,458,066 | A | 7/1984 | Caruthers et al. |
| 4,500,707 | A | 2/1985 | Caruthers et al. |
| 5,153,319 | A | 10/1992 | Caruthers |
| 5,449,769 | A * | 9/1995 | Bhatt ............ 536/25.3 |
| 5,869,643 | A | 2/1999 | Chatelain et al. |
| 6,114,519 | A | 9/2000 | Cole |
| 6,242,591 | B1 | 6/2001 | Cole |
| 7,227,015 | B2 | 6/2007 | Cole |
| 7,378,516 | B2 | 5/2008 | Cole et al. |

FOREIGN PATENT DOCUMENTS

| EP | 0294196 | 12/1998 |
| NL | 8902521 | 5/1991 |

OTHER PUBLICATIONS

Duthaler et al. J. Am. Chem. Soc., 1978, 100(16), p. 4969-4973.*
Agrawal, Sudhir et al., "Efficient Synthesis of Oligoribonucleotide and Its Phosphorothioate", Tetrahedron Letters, vol. 31. No. 52 1990, 7541-7544.
Caruthers, M. H. , "Gene synthesis machines: DNA chemistry and its uses", American Association for the Advancement of Science Oct. 18, 1985 , 281-285.
Cheruvallath, Zacharia S. et al., "Use of Phenylacetyl Disulfide (PADS) in the Synthesis of Oligodeoxyribonucleotide Phosphorothioates", Nucleosides & Nucleotides, 18(3), 1999-03-01, 485-492.

Eckstein, Fritz et al., "Phosphorothioates in molecular biology", TBS Mar. 14, 1989 , 97-100.
Hunkapiller, M. et al., "A microchemical facility for the analysis and synthesis of genes and proteins", Nature vol. 310 Jul. 12, 1984 1994-07-12 , 105-111.
"PADS/NMP for sulfurization of oligonucleotides", an IP.com publication, IPCOM000114760D Mar. 29, 2005 , 1-2.
Kamer, P.C.J. et al., "An Efficient Approach Toward the Synthesis of Phosphorothioate Diesters Via the Schonberg Reaction", Tetrahedron letters, vol. 30, No. 48 Sep. 15, 1989 , 6757-6760,1989.
Knorre, Dimitri K. et al., "Design and Targeted Reaction of Oligonucleotide Derivatives", CRC Press, Boca Raton, Fla , 101-151.
Itakura, Keiichi et al., "Synthesis and Use of Synthetic Oligonucleotides", Ann. Rev. Biochem. /984.53 1984 , 323-356.
Krotz, Achim H. et al., "Phosphorothloate Oligonucleotides with Low Phosphate Diester Content: Greater than 99.9% Sulfurization Efficiency with "Aged" Solutions of Phenylacetyl Disulfide (PADS)", Organic Process Research $ Dev 2004 , 852-858.
Lang, M et al., "The Penems, a New Class of ‚&Lactam Antibiotics. 2. Tota Representatives Synthesis of Racemic 6-Unsubstituted", Am Chem Society 101:21 Oct. 10, 1979 , 6296-6301.
Matteucci, M. D. et al., "Synthesis of Deoxyoligonucleotides on a Polymer Support", J. Am. Chem. Soc., vol. 103, No. 11 1981 , 3185-3191.
Pollak, Peter et al., "Nitriles", Wiley-VCH Verlag GmbH & Co. CGaA, 2002 , 1-15.
Sjoberg, Bertil et al., "Synthesis of Some Thiolacetic Acid Derivatives II. Phenyl- and 1-Naphthylthiol-acetic Acids", Acta Chem. Scand. 16 No. 5 1959 , 1036-1037.
Stec, Wojciech J et al., "Automated Solid-Phase Synthesis, Separation, and Stereochemistry of Phosphorothioate Analogues of Oligodeoxyribonucleotide", J. Am. Chem. Soc. 106 Oct. 1, 1984 , 6077-6079.
Tullo, Alex , "A Solvent Dries Up: Acetonitrile is in short supply, and chemistsa re concerned", Chemical & Engineering News: Business, vol. 86, No. 47, Nov. 24, 2008 ISSN 0009-2347 Nov. 24, 2008 , 27.
Vu, Huynh et al., "Internucleotide Phosphite Sulfurization With Tetraethylthiuram Disulfide. Phosphorothioate Oligonucleoitide Synthesis Via Phosphoramidite Chemistry", Tetrahedron Letters, vol. 32, No. 26 1991 , 3005-3008.
Wyrzykiewicz Tadeusz K. et al., "Efficiency of Sulfurization in the Synthesis of Oligodeoxyribonucleotide Phosphorothioates Utilizing Various Sulfurizing Reagents", Bioorganic & Medicinal Chmistry Letters, vol. 4, No. 12 1994 , 1519-1522.
Zon, Gerald et al., "Phosphorothioate oligonucleotides", Oligonucleotides and Analogues a practical Approach, IRL Press, Oxford 1991.
European Patent Office, Communication with Search Report dated Oct. 8, 2010.
Ghisaidoobe, Amar et al., "A two-step sulfurization for efficient solution-phase synthesis of phosphorothioate oligonucleotides", Science Direct Tetrahedron Letters 49 (2008) 3129-3132, Oct. 10, 2008, The Netherlands.
Zhang, Zhaoda et al., "Solid Phase Synthesis of Oligonucleotide Phosphorotioate Analogues Using Bis (ethoxythiocarbonyl)-tetrasulfide as a new Sulfur-Transfer Reagent", Tetrahedron Letters 39 (1998) 2467-2470, Feb. 5, 1998.

* cited by examiner

*Primary Examiner* — Shaojia Anna Jiang
*Assistant Examiner* — Jonathan S Lau

(57) ABSTRACT

A method and compositions for sulfurizing at least one phosphite or thiophosphite linkage in an oligonucleotide. The addition of N-alkyl imidazole to the acetyldisulfide sulfurization solution enables the use of industrially preferred solvents or solvents that are derived from renewable resources.

21 Claims, 12 Drawing Sheets

Figure 1:
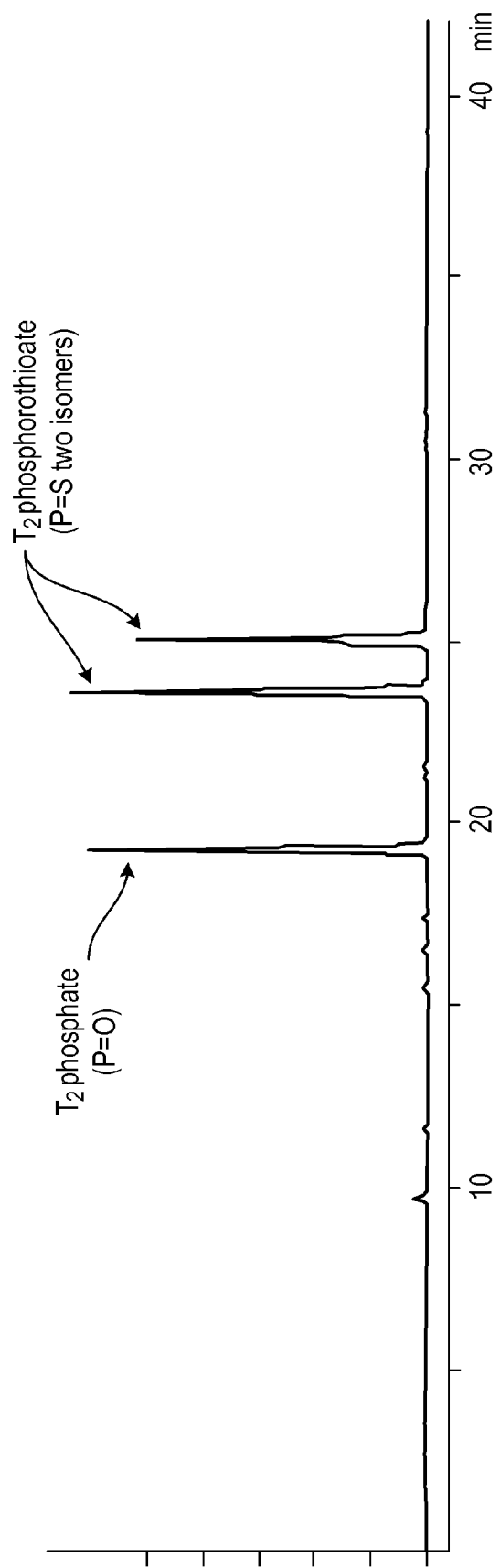

USE OF N-ALKYL IMIDAZOLE FOR SULFURIZATION OF OLIGONUCLEOTIDES WITH AN ACETYL DISULFIDE

FIELD

Methods and compositions for synthesizing sulfurized oligonucleotides are disclosed.

INTRODUCTION

Modified oligonucleotides find use in a variety of applications, including research, diagnostic and therapeutic applications. In particular, with respect to therapeutic applications, the modified oligonucleotides find use as any DNA, RNA or other nucleic acid therapeutic, such as antisense nucleic acids, in gene therapy applications, aptamers and more recently interfering RNA (i.e., iRNA or RNAi) applications, etc.

Phosphorothioate analogues, in particular, are of considerable interest in nucleic acid research, diagnostics and therapeutics (Eckstein, F. and Gish, G. (1989) TIBS, 14, 97-100). The substitution of a sulfur atom for a non-bridging oxygen atom significantly changes the ability of the internucleotide bond to be degraded by cellular nucleases (Zon, G. and Stec, W. J. (1991) In Eckstein, F. (ed.), Oligonucleotides and Analogues: A Practical Approach. IRL Press, Oxford, pp. 87-108.)

Introduction of phosphorothioate moieties into oligonucleotides, assembled by solid-phase synthesis, can be achieved readily in two ways. The H-phosphonate approach involves a single sulfur transfer step, carried out after the desired sequence has been assembled, to convert all of the internucleotide linkages to phosphorothioates (Agrawal, S, and Tang, J.-Y. Tetrahedron Lett., 31, (1990) 7541-7544).

Alternatively, the phosphoramidite approach (Matteucci, M. D., Caruthers, M. H. J. Am. Chem. Soc., 103, (1981), 3186-3191) features a choice at each synthetic cycle: a standard oxidation using iodine and water provides the normal phosphodiester internucleotide linkage, whereas a sulfurization step introduces a phosphorothioate at that specific position in the sequence (Stec, W. J., Zon, G., Egan, W. and Stec, B., J. Am. Chem. Soc., 106, (1984), 6077-6079). An advantage of using phosphoramidite chemistry, therefore, is the capability to control the state of each linkage [P=O versus P=S] in a site-specific manner.

Phenylacetyl disulfide (PADS) was shown to be an effective sulfur transfer reagent and its rate of sulfurization appeared rapid (5 minutes) similar to the 3-H-12-benzodithiol-3-one 1,1-dioxide, known as the "Beaucage Reagent" (Kamer, P. C. J., Roelen, H. C. P. F, van den Elst, H., Van Der Marel, G. A, and Van Boom J. H., Tetrahedron Lett., 30, (1989) 6757-6760). However, most published reports of its use were in chlorinated solvents with moderate to high dielectric constants such as dichloroethane; which are non-preferred for large, industrial-scale synthesis due to the environmental concerns of exposure and disposal of haloalkane solvents. The use of PADS reagent for sulfurization of nucleotides and oligonucleotides in a mixture of dichloroethane, acetonitrile, and pyridine was described in a 1991 Dutch patent application (NL8902521 (A); Production of phosphorothioate ester—by reacting phosphite ester with acyl disulphide, especially in synthesis of nucleic acid analogues). In this patent application the use of PADS was demonstrated for sulfurization of mononucleotides, dinucleotides and short oligonucleotides (6 and 7 nucleotides in length). Subsequently, the use of PADS for the synthesis of an oligonucleotide, 20 nucleotides in length, was demonstrated using a mixture of dichloroethane and collidine (Wyrzykiewicz, T. K., and Ravikumar, V. T., Bioorganic & Medicinal Chemistry Letters (1994), 4(12), 1519-22). Following this account, it was reported that, similar to tetraethylthiuram disulfide (TETD), PADS was more effective as a sulfur transfer reagent when dissolved in higher dielectric constant solvents such as acetonitrile (Cheruvallath, Z. S.; Wheeler, P. D.; Cole, D. L.; Ravikumar, V. T., Nucleosides, Nucleotides and Nucleic Acids, (1999) 18, 485-492; Synthesis of Sulfurized Oligonucleotides: U.S. Pat. No. 7,378,516 B2, 05/2008, D. L. Cole, V. T. Ravikumar, Z. S. Cheruvallath). It has also been recently disclosed that PADS can be used in 50/50:v/v mixtures of 3-picoline with a variety of organic co-solvents such as acetonitrile, toluene, 1-methylpyrrolidinone, and tetrahydrofuran (PADS/NMP for sulfurization of oligonucleotides, IP.com Journal (2005), 5(4), pp 69-70).

Acetonitrile is a by-product from the manufacture of acrylonitrile (Peter Pollak, Gérard Romeder, Ferdinand Hagedorn, Heinz-Peter Gelbke "Nitriles" in Ullmann's Encyclopedia of Industrial Chemistry, Wiley-VCH, 2002: Weinheim). Production trends for acetonitrile thus generally follow those of acrylonitrile. Acetonitrile can also be produced by many other methods, but these are currently of no commercial importance and are not used to produce commercial amounts of acetonitrile. As of October 2008, there has been a decrease of acetonitrile production due to decreased production of acrylonitrile (Chemical & Engineering News, (2008) 86:47, p. 27). The shortage arose from a lower output from China and a U.S. factory in Texas damaged during Hurricane Ike. The global economic slowdown of 2007, 2008, and 2009 has affected the demand and the production of acrylonitrile which is used in the manufacture of acrylic fibers and acrylonitrile-butadiene (ABS) resins. Along with the lack of availability, the price of acetonitrile has significantly increased.

In the community of Large Scale Oligonucleotide Manufacturing, PADS is found to be an efficient sulfurization reagent available at a reasonable cost, but is taught to be preferably used in acetonitrile containing solution (Isis U.S. Pat. No. 6,114,519, U.S. Pat. No. 6,242,591, U.S. Pat. No. 7,227,015, U.S. Pat. No. 7,378,516). In the last two years, however, the industrial decrease in acetonitrile production and its associated cost increase have prompted the Oligonucleotide Manufacturing community to look at alternative solvents and conditions to use PADS.

SUMMARY

Aspects of this invention include new compositions and methods to produce phosphorothioate or phosphorodithioate linkages containing oligonucleotides.

DEFINITIONS

Prior to describing embodiments of the invention in further detail, the terms used in this application are defined as follows unless otherwise indicated.

An "acetyl disulfide" has the formula $R^{20}$—C(O)—S—S—C(O)—$R^{21}$ where $R^{20}$ and $R^{21}$ may be the same or different substituents, such as hydrocarbyl (for example, C1 to C12 alkyl or aryl, such as phenyl or napthyl), any of which may be substituted or unsubstituted (for example, with lower alkyl, halo, amino or the like). When $R^{20}$ and $R^{21}$ are both phenyl, the compound is phenyl acetyl disulfide.

The term "alkyl" as used herein, unless otherwise specified, refers to a saturated straight chain, branched or cyclic hydrocarbon group of 1 to 24, typically 1-12, carbon atoms, such as methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "lower alkyl" intends an alkyl group of one to six carbon atoms, and includes, for example, methyl, ethyl, n-propyl, isopropyl, n-butyl, isobutyl, t-butyl, pentyl, cyclopentyl, isopentyl, neopentyl, hexyl, isohexyl, cyclohexyl, 3-methylpentyl, 2,2-dimethylbutyl, and 2,3-dimethylbutyl. The term "cycloalkyl" refers to cyclic alkyl groups such as cyclopropyl, cyclobutyl, cyclopentyl, cyclohexyl, cycloheptyl and cyclooctyl.

The term "aryl" refers to 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The term "aryl" also includes polycyclic ring systems having two or more cyclic rings in which two or more carbons are common to two adjoining rings (the rings are "fused rings") wherein at least one of the rings is aromatic (e.g., the other cyclic rings may be cycloalkyls, cycloalkenyls, cycloalkynyls, aryls, and/or heterocycles). A "lower aryl" contains up to 18 carbons, such as up to 14, 12, 10, 8 or 6 carbons.

The term "hydrocarbyl" refers to alkyl, alkenyl or alkynyl. The term "substituted hydrocarbyl" refers to hydrocarbyl moieties having substituents replacing a hydrogen on one or more carbons of the hydrocarbon backbone. Such substituents may include, for example, a hydroxyl, a halogen, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclic, an aralkyl, or an aromatic or heteroaromatic moiety. It will be understood by those skilled in the art that the moieties substituted on the hydrocarbon chain may themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CN, and the like. Cycloalkyls may be further substituted with alkyls, alkenyls, alkoxys, alkylthios, aminoalkyls, carbonyl-substituted alkyls, —CN, and the like.

A "nucleotide" or "nucleotide moiety" refers to a sub-unit of a nucleic acid (whether DNA or RNA or analogue thereof) which includes a phosphate group, a sugar group and a heterocyclic base, as well as analogs of such sub-units. Other groups (e.g., protecting groups) can be attached to any component(s) of a nucleotide.

A "nucleoside" or "nucleoside moiety" references a nucleic acid subunit including a sugar group and a heterocyclic base, as well as analogs of such sub-units. Other groups (e.g., protecting groups) can be attached to any component(s) of a nucleoside.

The terms "nucleoside" and "nucleotide" are intended to include those moieties that contain not only the known purine and pyrimidine bases, e.g. adenine (A), thymine (T), cytosine (C), guanine (G), or uracil (U), but also other heterocyclic bases that have been modified. Such modifications include methylated purines or pyrimidines, acylated purines or pyrimidines, alkylated riboses or other heterocycles. Such modifications include, e.g., diaminopurine and its derivatives, inosine and its derivatives, alkylated purines or pyrimidines, acylated purines or pyrimidines thiolated purines or pyrimidines, and the like, or the addition of a protecting group such as acetyl, difluoroacetyl, trifluoroacetyl, isobutyryl, benzoyl, 9-fluorenylmethoxycarbonyl, phenoxyacetyl, dimethylformamidine, dibutylformamidine, dimethylacetamidine, N,N-diphenyl carbamate, or the like. The purine or pyrimidine base may also be an analog of the foregoing; suitable analogs will be known to those skilled in the art and are described in the pertinent texts and literature. Common analogs include, but are not limited to, 1-methyladenine, 2-methyladenine, N6-methyladenine, N6-isopentyladenine, 2-methylthio-N-6-isopentyladenine, N,N-dimethyladenine, 8-bromoadenine, 2-thiocytosine, 3-methylcytosine, 5-methylcytosine, 5-ethylcytosine, 4-acetylcytosine, 1-methylguanine, 2-methylguanine, 7-methylguanine, 2,2-dimethylguanine, 8-bromoguanine, 8-chloroguanine, 8-aminoguanine, 8-methylguanine, 8-thioguanine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)uracil, 5-(methylaminomethyl)uracil, 5-(carboxymethylaminomethyl)-uracil, 2-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 2-aminopurine, 6-hydroxyaminopurine, 6-thiopurine and 2,6-diaminopurine.

In addition, the terms "nucleoside" and "nucleotide" include those moieties that contain not only conventional ribose and deoxyribose sugars and conventional stereoisomers, but other sugars as well, including L enantiomers and alpha anomers. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features such that they can be considered mimetics, derivatives, having analogous structures, or the like, and include, for example, polynucleotides or oligonucleotides incorporating non-natural (not usually occurring in nature) nucleotides, unnatural nucleotide mimetics such as 2'-modified nucleosides including but not limited to 2'-fluoro, 2'-O-alkyl, O-alkylamino, O alkylalkoxy, protected O-alkylamino, O-alkylaminoalkyl, O-alkyl imidazole, and polyethers of the formula (O-alkyl)m such as linear and cyclic polyethylene glycols (PEGs), and (PEG)-containing groups, locked nucleic acids (LNA), peptide nucleic acids (PNA), oligomeric nucleoside phosphonates, and any polynucleotide that has added substituent groups, such as protecting groups or linking groups.

An "internucleotide linkage" or "nucleotide bond" refers to a chemical linkage between two nucleoside moieties, such as the phosphodiester linkage in nucleic acids found in nature or their thiolated or dithiolated equivalents, or linkages well known from the art of synthesis of nucleic acids and nucleic acid analogues. An internucleotide bond may include a phospho or phosphite group, and may include linkages where one or more oxygen atoms of the phospho or phosphite group are either modified with a substituent or replaced with another atom, e.g., a sulfur atom, or the nitrogen atom of a mono- or di-alkyl amino group.

An "N-alkyl imidazole" can include lower N-alkyl imidazoles. In this context "lower" means C1 to C6 in total, unsubstituted or substituted.

A "phospho" group includes a phosphodiester, phosphotriester, and H-phosphonate groups. In the case of either a phospho or phosphite group, a chemical moiety other than a substituted 5-membered furyl ring may be attached to O of the phospho or phosphite group which links between the furyl ring and the P atom.

"Phosphite" is a compound which includes a $P(OR)_3$, where R is a group many of which are known, and includes structures that may be related such as by disproportionation. A "phoshite" then includes an H-phosphonate, namely $HP(O)(OR)_2$.

The term "phosphoramidite group" refers to a group comprising the structure —P—$(OR^{13})(NR^{14}R^{15})$—, wherein each of $R^{13}$, $R^{14}$, and $R^{15}$ is independently a hydrocarbyl, substituted hydrocarbyl, heterocycle, substituted heterocycle, aryl or substituted aryl. In some embodiments, $R^{13}$, $R^{14}$, and $R^{15}$ may be independently selected from aryls, alkyls, any of which may be substituted or unsubstituted. Any of $R^{13}$, $R^{14}$, or $R^{15}$ may, for example, include structures containing up to 18, 16, 14, 12, 11, 10, 9, 8, 7, 6, 5, 4, 3 or 2 carbons. In some embodiments, $R^{13}$ is 2-cyanoethyl or methyl, and either or both of $R^{14}$ and $R^{15}$ is isopropyl. $R^{14}$ and $R^{15}$ can optionally be cyclically connected.

The term "phosphothioamidite group" refers to a group comprising the structure —P—$(SR^{13})(NR^{14}R^{15})$, wherein each of $R^{13}$, $R^{14}$, and $R^{15}$ is independently selected from any of those groups already mentioned for $R^{13}$, $R^{14}$, and $R^{15}$.

The term "Phosphorohioate" usually refers to an analogue of a phosphodiester or phosphotriester linkage in which a non-bridging oxygen has been replaced by a sulfur atom comprising the structure O—P(S)(OR)—O— or —O—P(S)(O⁻)—O—, wherein R is a substituent such as a substituted or unsubstituted alkyl or aryl group.

The term "Phosphorodithioate" refers to an analogue of phosphodiester or phosphotriester linkage in which both of the non-bridging oxygen have been replaced by a sulfur atom comprising the structure —O—P(S)(SR)—O— or —O—P(S)(S⁻)—O—, wherein R is a substituent such as a substituted or unsubstituted alkyl or aryl group.

An "oligonucleotide", "polynucleotide" or a "nucleic acid" refers to a compound containing a plurality of nucleoside moiety subunits or nucleoside residues that are linked by internucleotide bonds. As such it also refers to a compound containing 2'-deoxynucleotide or ribonucleotide, or nucleotide analogue subunits or mixture thereof. Oligonucleotides may typically have more than 2, 10, 20, or 30 nucleotides up to any number of nucleotides (for example, up to 10, 20, 40, 60, 80, 100, or 200 nucleotides).

"Linkage" as used herein refers to a first moiety bonded to two other moieties, wherein the two other moieties are linked via the first moiety. Typical linkages include ether (—O—), oxo (—C(O)—), amino (—NH—), amido (—N—C(O)—), thio (—S—), phospho (—P—), ester (—O—C(O)—).

"Low dielectric constant" means a dielectric constant (measured at 20° C.) which is 35 or less, and could even be 32 or less, 25 or less, 20 or less, 15 or less, 10 or less, or 1 or less. A "low dielectric constant solvent" is a solvent with a low dielectric constant.

"High dielectric constant solvent" references a solvent having a dielectric constant of greater than 35 as measured at 20° C. including 37 or greater, or even greater than 40. High dielectric constant solvents are preferably aprotic solvents.

A "solvent" can be made up of a single solvent or multiple solvents. Sometimes "solvent" is used interchangeably herein within "solvent system".

The term "substituted" as used to describe chemical structures, groups, or moieties, refers to the structure, group, or moiety comprising one or more substituents. As used herein, in cases in which a first group is "substituted with" a second group, the second group is attached to the first group whereby a moiety of the first group (in some cases a hydrogen) is replaced by the second group.

"Substituent" references a group that replaces another group in a chemical structure. In some cases substituents include nonhydrogen atoms (e.g. halogens), functional groups (such as, but not limited to amino, amido, sulfhydryl, carbonyl, hydroxyl, alkoxy, carboxyl, silyl, silyloxy, phosphate and the like), hydrocarbyl groups, and hydrocarbyl groups substituted with one or more heteroatoms.

Hyphens, or dashes are used at various points throughout this specification to indicate attachment, e.g. where two named groups are immediately adjacent to a dash in the text, this indicates that the two named groups area attached to each other. Similarly, a series of named groups with dashes between each of the named groups in the text indicated the named groups are attached to each other in the order shown. Also, a single named group adjacent a dash in the text indicates that the named group is typically attached to some other, unnamed group. The attachment indicated by a dash generally represents a covalent bond between the adjacent named groups. At various points throughout the specification, a group may be set forth in the text with or without an adjacent dash, (e.g. amido or amido-, further e.g. alkyl or alkyl-, yet further Lnk, Lnk- or -Lnk-) where the context indicates the group is intended to be (or has the potential to be) bound to another group; in such cases, the identity of the group is denoted by the group name (whether or not there is an adjacent dash in the text). Note that where context indicates, a single group may be attached to more than one other group (e.g., where a linkage is intended, such as linking groups).

"Bound" may be used herein to indicate direct or indirect attachment. In the context of chemical structures, "bound" (or "bonded") may refer to the existence of a chemical bond directly joining two moieties or indirectly joining two moieties (e.g. via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and also embodiments where the attachment is indirect. "Free," as used in the context of a moiety that is free, indicates that the moiety is available to react with or be contacted by other components of the solution in which the moiety is a part.

When any range of numbers is mentioned herein, every number within the range (particularly every whole number) is specifically included herein. For example, a range of 1 to 14 C atoms specifically includes 1, 2, 3, 4, 5, 6, 7, 8, 9, 10, 11, 12, 13, and 14 C atoms.

DRAWINGS

Embodiments of the invention will now be described with reference to the drawings, in which:

FIG. 1: RP-HPLC chromatogram of a TT dimer phosphorothioate and a TT dimer phosphate.

Figure 2:
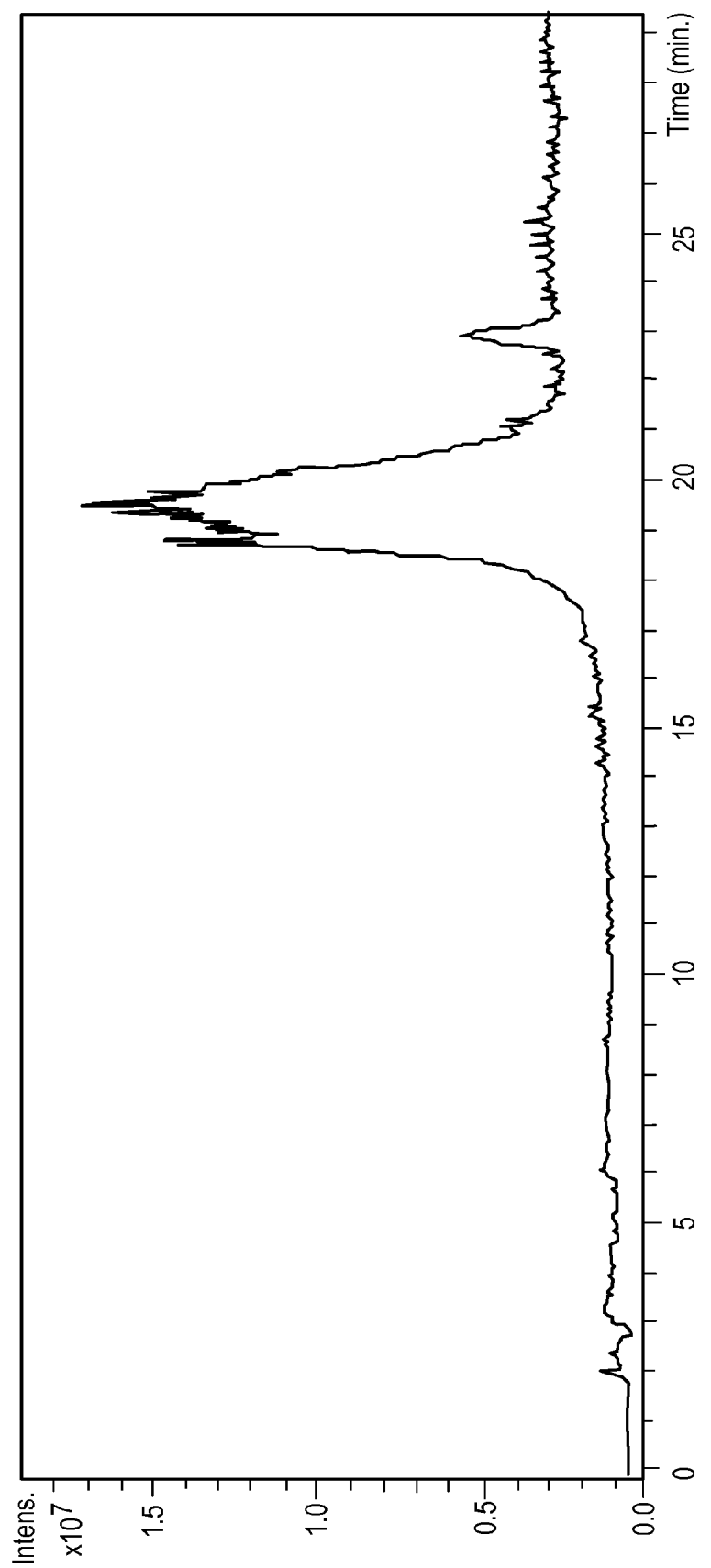

FIG. 2: Total Ion Chroamtogram (TIC) obtained from Ion Trap LC/mass spectrometry analysis of a 13-mer DNA phosphorothioate thioalated with 0.2M PADS in propylene carbonate/NMI:90/10: v/v.

Figure 3A:
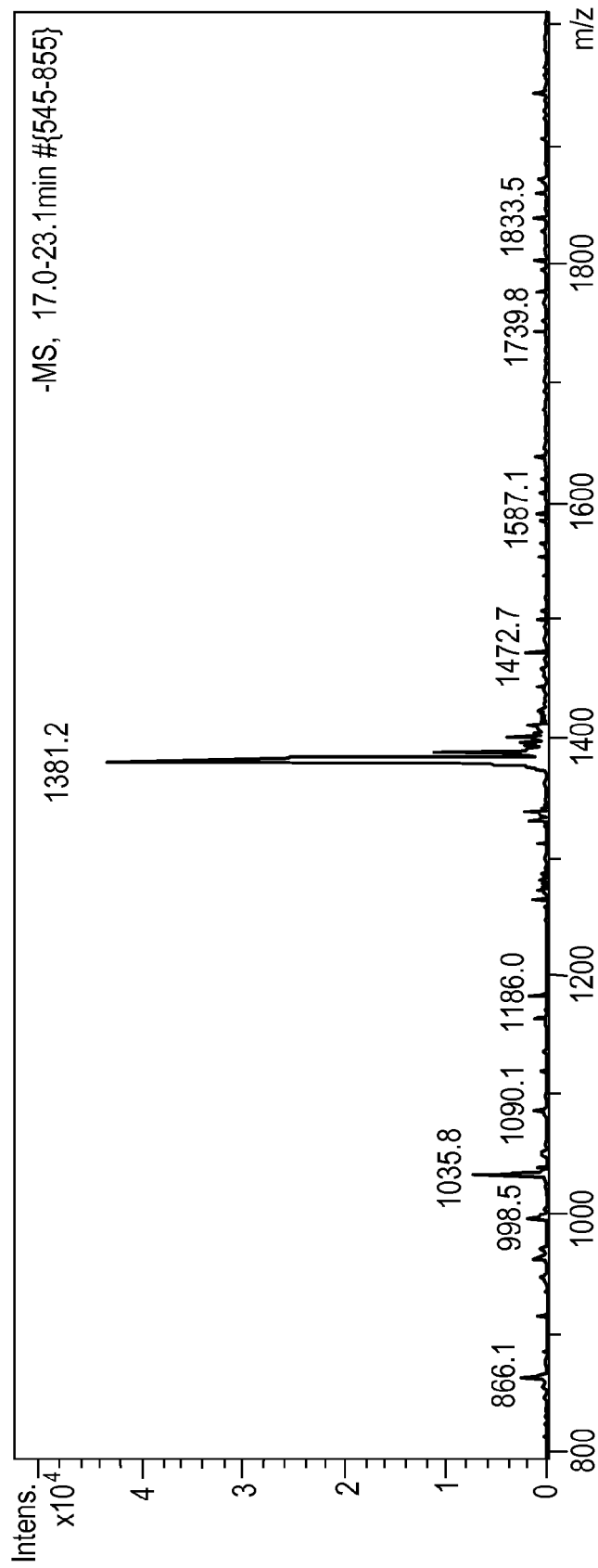
Figure 3B:
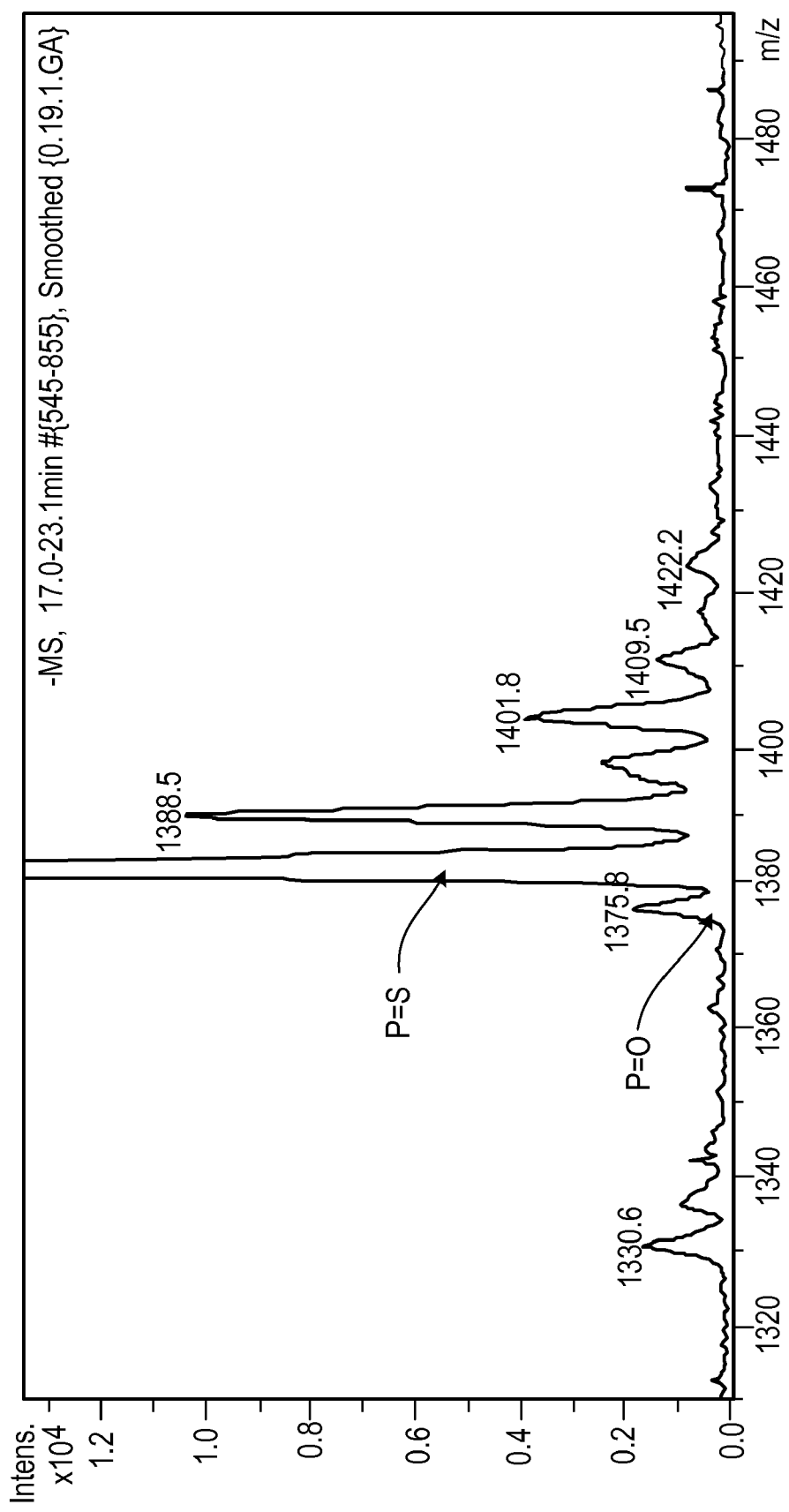

FIGS. 3a and 3b: Ion Trap LC/MS chromatograms of a 13-mer DNA phosphorothioate thioalated with 0.2M PADS in propylene carbonate/NMI:90/10:v/v. From these chromatograms and tabulated data, it is possible to determine the total amount (in %) of P=O oligonucleotide that contaminates the 13-mer DNA phosphorothioate oligonucleotide thioalated with 0.2M PADS in propylene carbonate/NMI:90/10:v/v.

Figure 4:
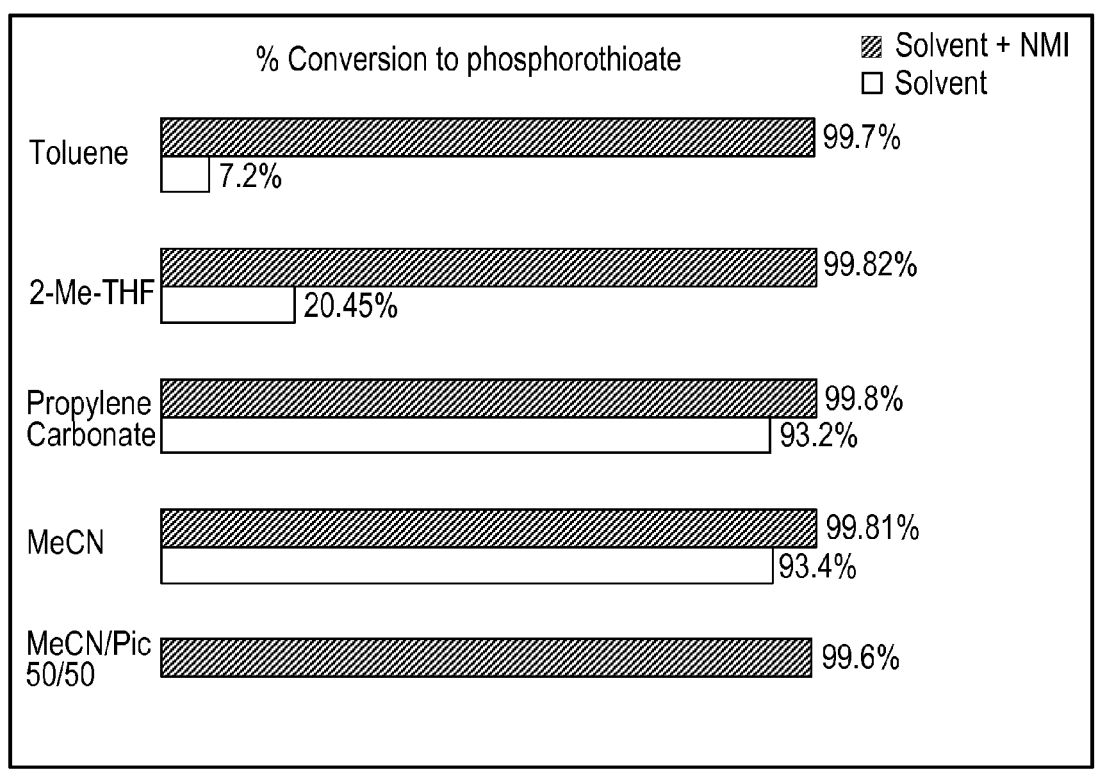

FIG. 4: Comparison of a TT dimer thiolation efficiency performed with a 0.2M PADS solution prepared with different solvent in the presence (or absence) of 10% N-methyl imidzaole (v/v).

Figure 5:
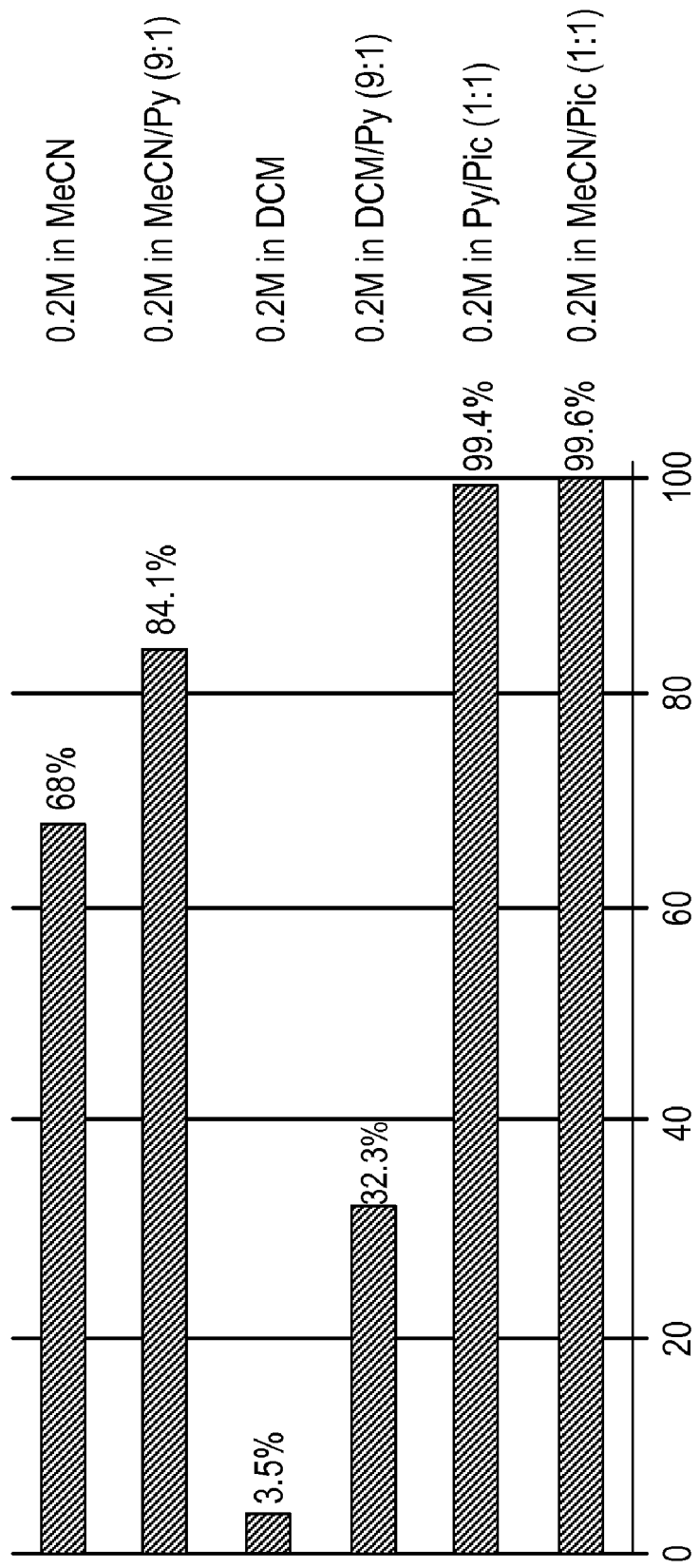

FIG. 5: Comparison of TT dimer thiolation efficiency performed with 0.2M PADS in different solvents (no N-alkyl imidazole).

Figure 6A:
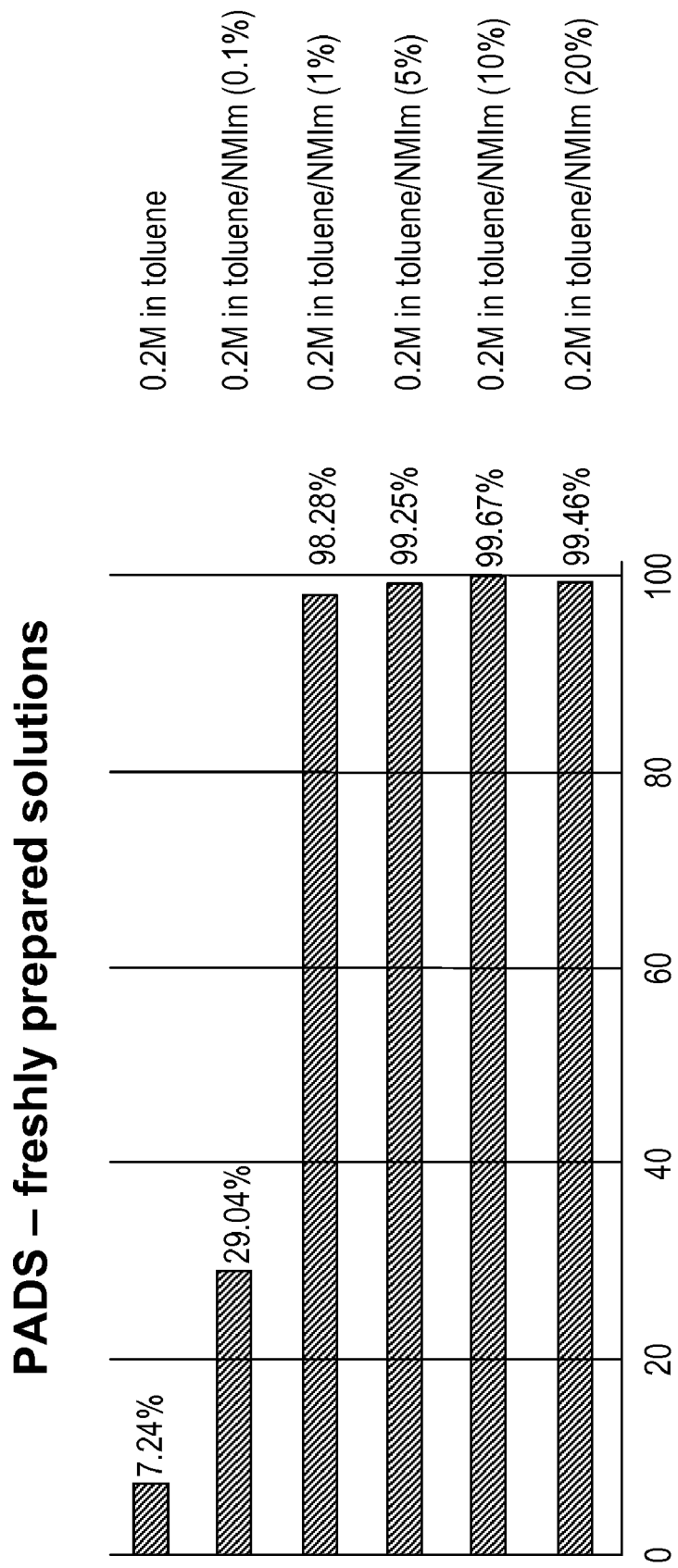
Figure 6B:
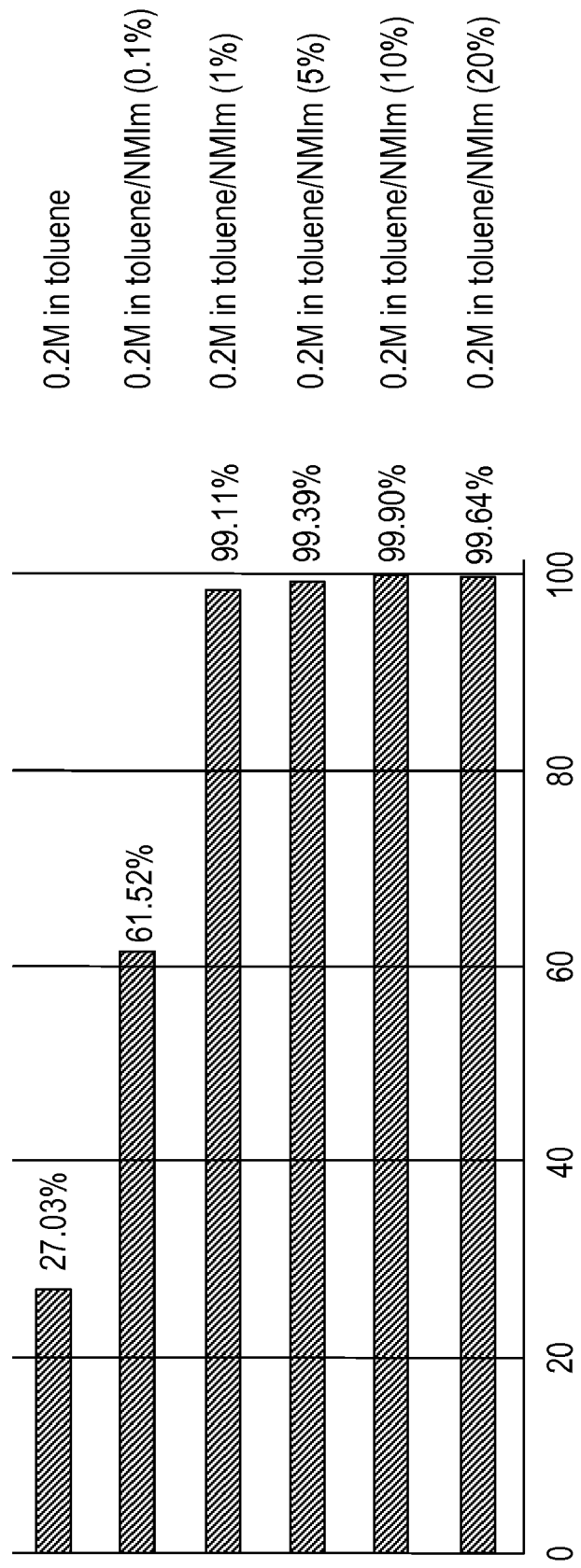

FIGS. 6a and 6b: Comparison of TT dimer thiolation efficiency performed with 0.2M PADS in various toluene/N-methyl imidazole solutions freshly prepared (6a) or aged for 24 hrs (6b).

Figure 7A:
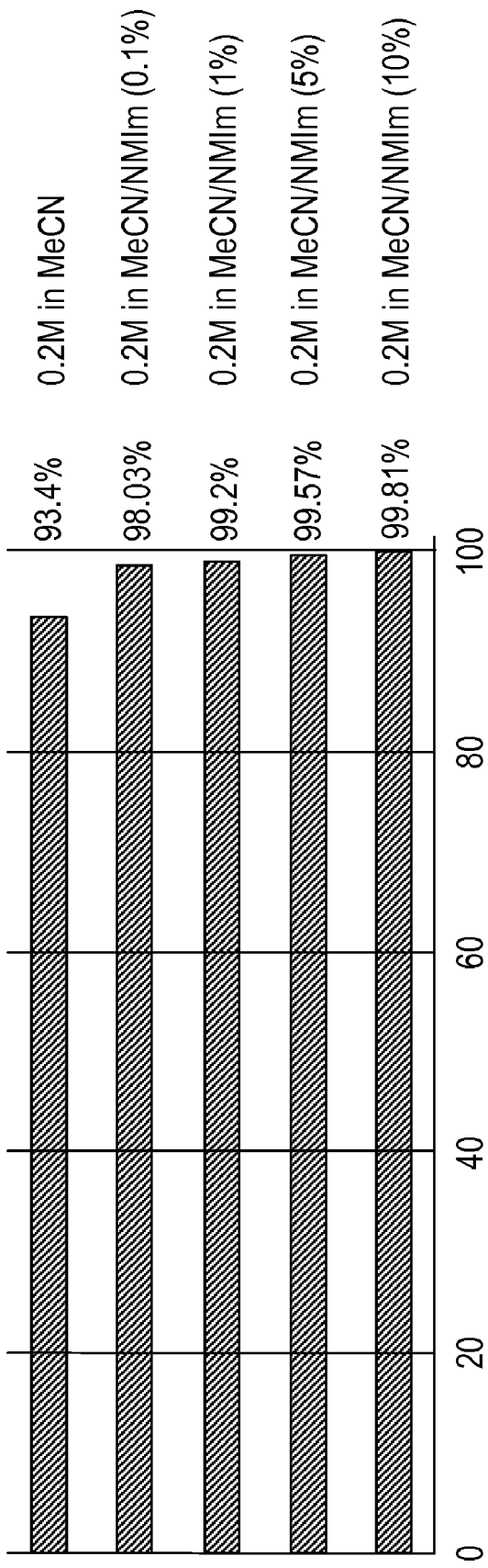
Figure 7B:
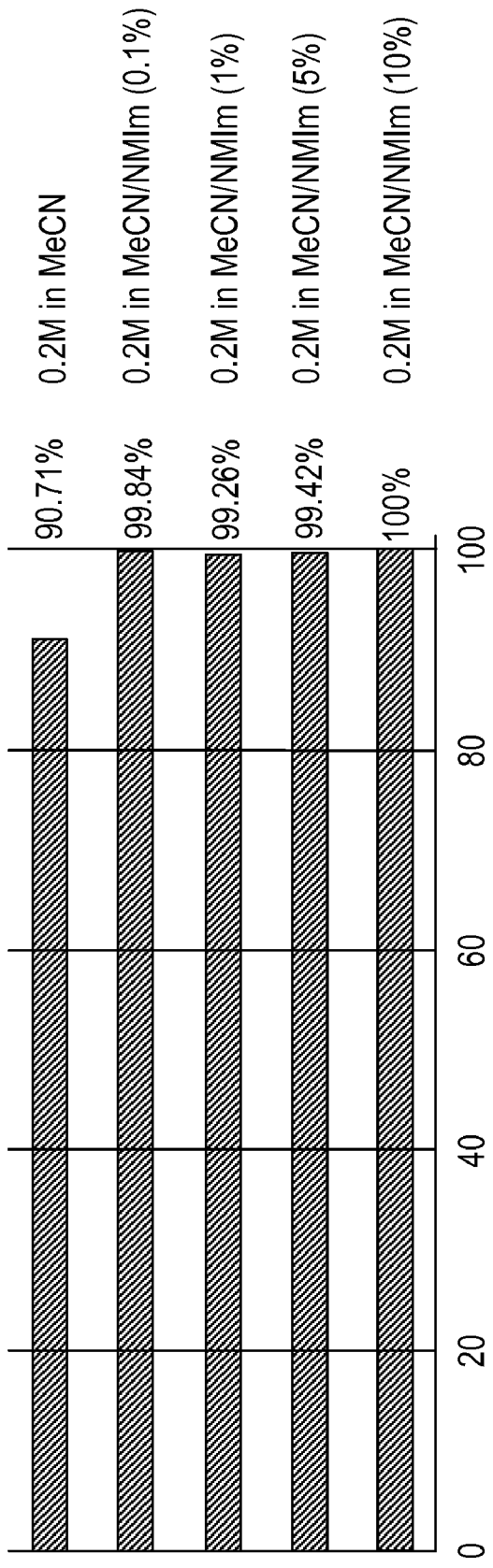

FIGS. 7a and 7b: TT Comparison of dimer thiolation efficiency performed with 0.2M PADS in various MeCN/N-methyl imidazole solutions freshly prepared (7a) or aged for 24 hrs (7b).

Figure 8A:
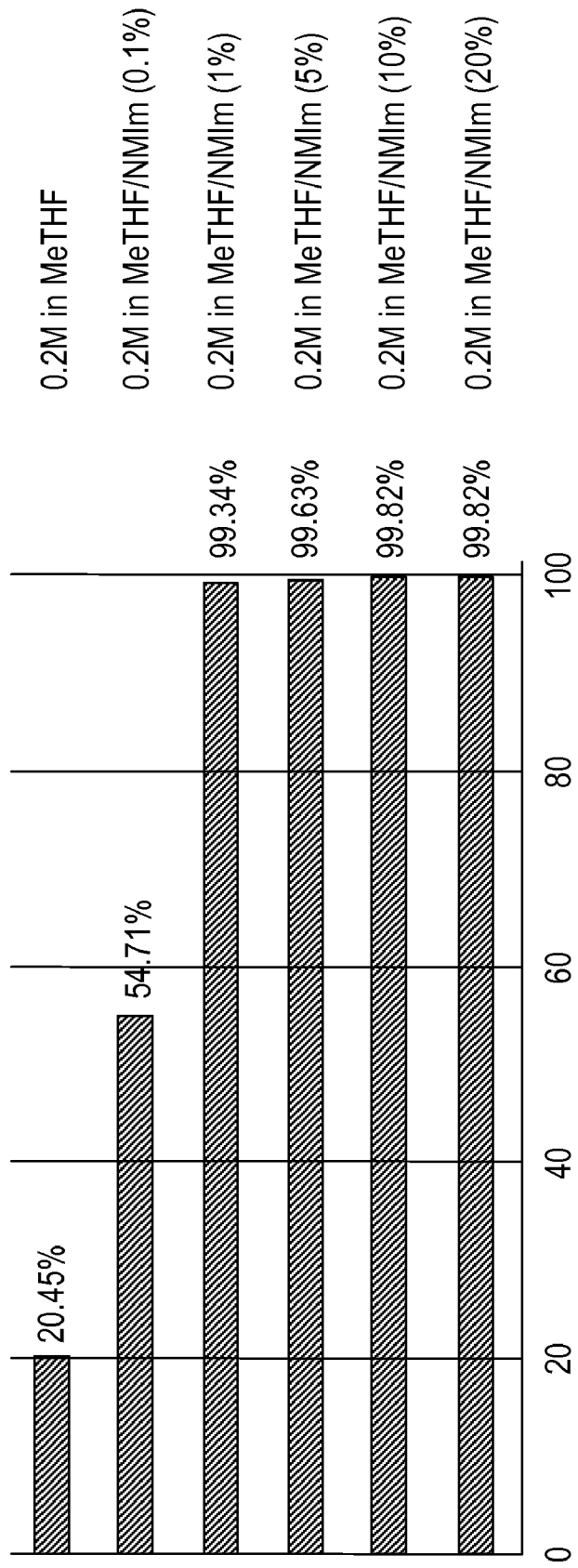
Figure 8B:
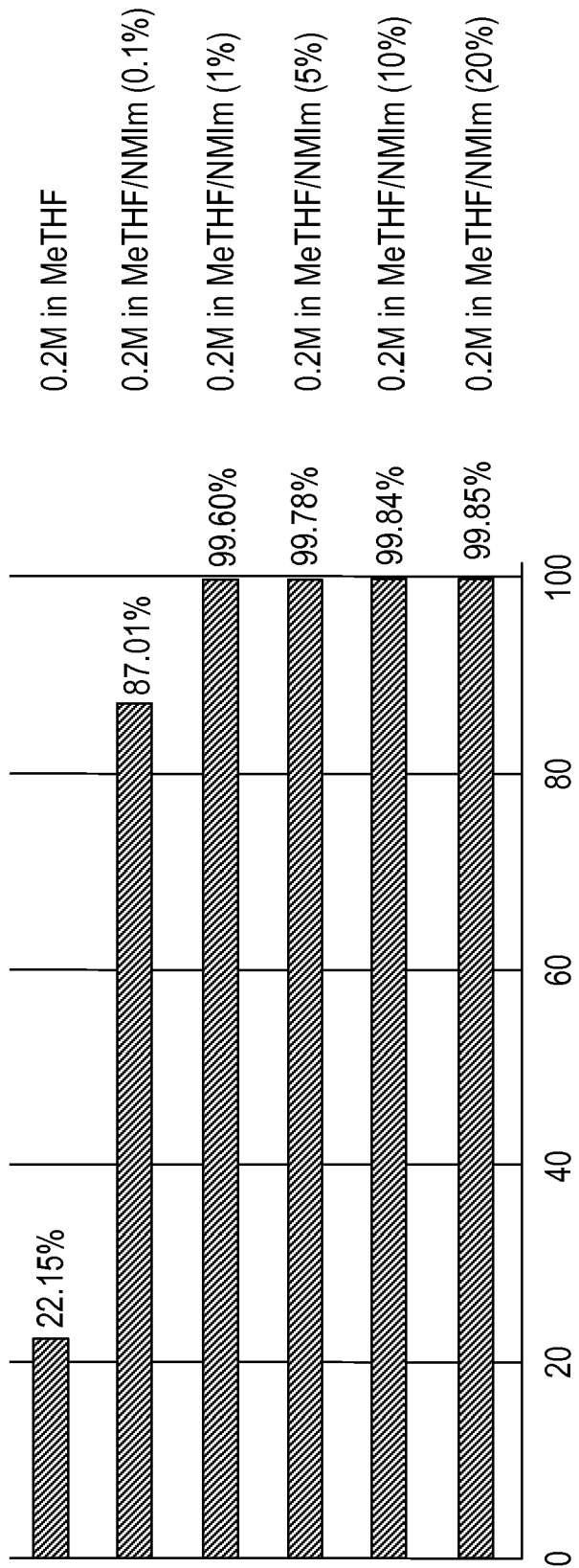

FIGS. 8a and 8b: Comparison of TT dimer thiolation efficiency performed with 0.2M PADS in various 2-Methyl THF/N-methyl imidazole solutions freshly prepared (8a) or aged for 24 hrs (8b).

DETAILED DESCRIPTION

The following examples illustrate the synthesis of some compounds of the present invention, and are not intended to limit the scope of the invention set forth in the claims appended hereto.

A method of producing a phosphorothioate or a phosphorodithioate internucleotide linkage into an oligonucleotide, is provided. In some embodiments, the method comprises:
providing a phosphite or a thiophosphite intermediate
contacting said phosphite or thiophosphite intermediate with a composition comprising an acetyl disulfide, a solvent and a N-alkyl imidazole for a time sufficient to convert said phosphite or thiophosphite intermediate to said phosphorothioate or phosphorodithioate internucleotide linkage.

In certain embodiments, the method of producing a phosphorothioate or a phosphorodithioate linkage in an oligonucleotide, comprises:
providing a phosphite or a thiophosphite intermediate
contacting said phosphite or thiophosphite intermediate with a composition comprising phenylacetyl disulfide, a solvent and N-methyl imidazole for a time sufficient to convert said phosphite or thiophosphite intermediate to said phosphorothioate or phosphorodithioate internucleotide linkage.

In other embodiments of the method described above, the solvent has a low dielectric constant.

In particular embodiments, the solvent comprises toluene, xylene, 2-methyl THF, cyclopentyl methyl ether, acetonitrile or propylene carbonate.

In embodiments of the invention the solvent may make up at least 30%, 50%, 60%, 80%, 90% or even 95% of the composition (in volume) used for contacting the phosphite or thiophosphite.

In particular embodiment of the described above sulfurization method, the solvent is toluene.

In another embodiment of the sulfurization method, the solvent is 2-methyl THF.

In some embodiments of the invention, the method of converting a phosphite or thiophosphite internucleotide linkage of an oligonucleotide to a phosphorothioate or phosphorodithioate is described wherein said N-alkyl imidazole is at least 1% in volume (v/v) in said solvent (or at least 5% or at least 10% (v/v) in said solvent). The N-alkyl imidazole may be up to 10%, 15%, or even 25% (v/v) in said solvent in some embodiments.

In some embodiments, the method of sulfurization features N-allyl imidazole at a concentration of at least 5% in volume (v/v) in said solvent.

In particular embodiments, the method of sulfurization is described wherein said acetyl disulfide is at least at 0.1M concentration in said solvent.

In certain embodiments of the of the sulfurization method described above, the phenylacetyl disulfide is at a concentration of at least 0.1 M and N-methyl imidazole is at least 5% in volume (v/v) in said solvent system.

In particular embodiments of the sulfurization method described above, the solvent system is toluene, phenylacetyl disulfide is at a concentration of at least 0.1 M and N-methyl imidazole is at least 5% in volume in toluene (v/v).

In particular embodiments of the sulfurization method described above, the solvent system is toluene, phenylacetyl disulfide reagent is at a concentration of 0.2 M and N-methyl imidazole is 10% to 20% in toluene (v/v).

In particular embodiments of the sulfurization method described above the solvent is 2-methyl THF, phenylacetyl disulfide is at a concentration of at least 0.1 M and N-methyl imidazole is at least 5% in volume in 2-methyl THF (v/v).

In particular embodiments of the sulfurization method described above, the solvent system is 2-methyl THF, phenylacetyl disulfide is at a concentration of 0.2 M and N-methyl imidazole is 10% to 20% in volume in 2-methyl THF (v/v).

In certain embodiments, a method of sulfurizing at least one phosphite or thiophosphite linkage intermediate in an oligonucleotide is described, said method comprising:
providing a phosphite or a thiophosphite intermediate bound to a solid support,
contacting said phosphite or thiophosphite intermediate with a composition comprising an acetyl disulfide, a solvent and N-alkyl imidazole for a time sufficient to convert said phosphite or thiophosphite intermediate to said phosphorothioate or phosphorodithioate.

In particular embodiments of the sulfurization method, the solid support is controlled pore glass or polystyrene.

In particular embodiments of said sulfurization method, the solid support is an array substrate or beads.

In some embodiments of the method further comprising a phosphite or thiophosphite intermediate attached to a solid support, the solvent is selected from toluene, xylene, 2-methyl THF, cyclopentyl methyl ether, acetonitrile and propylene carbonate.

In certain embodiments of the invention, the method is featured wherein N-methyl imidazole is at least at 5% in volume and phenylacetyl disulfide at least at 0.1 M concentration in said solvent.

In some embodiments of the sulfurization method described above, the oligonucleotide comprises one or more ribonucleotide.

In certain embodiments of the sulfurization method described above, the oligonucleotide comprises at least one nucleotide analogue.

A composition to thiolate a phosphite or thiophophite linkage intermediate in an oligonucleotide is provided. The composition comprises: phenylacetyl disulfide at a concentration of at least 0.1M and N-methyl imidazole at least at 5% in a solvent (v/v).

In particular embodiments, the composition comprises: toluene as a solvent, phenylacetyl disulfide at a 0.2 M concentration and N-methyl imidazole at 10% in toluene (v/v).

In particular embodiments, the composition comprises 2-methyl THF as a solvent, phenylacetyl disulfide at 0.2 M concentration and N-methylimidazole at 10% in 2-methyl THF (v/v).

An oligonucleotide containing at least one phosphorothioate or phosphorodithioate linkage produced by the method of the invention.

Oligonucleotide Synthesis.

The conventional sequence used to prepare an oligonucleotide using phosphoramidite chemistry basically follows the following steps (Matteucci, M. D., Caruthers, M. H. *J. Am. Chem. Soc.*, 103, (1981), 3186-3191): (a) coupling a selected nucleoside through a phosphite or thiophosphite linkage to a functionalized support in the first iteration, or to the 2', 3', or 5' positions of a nucleoside bound to the substrate (i.e. the nucleoside-modified substrate) in subsequent iterations (step (a) is sometimes referenced as "phosphitylating"); (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in a known manner.

The foregoing methods of preparing polynucleotides are described in detail, for example, in Caruthers, *Science* 230: 281-285, 1985; Itakura et al., *Ann. Rev. Biochem.* 53: 323-356; Hunkapillar et al., *Nature* 310: 105-110, 1984; and in "Synthesis of Oligonucleotide Derivatives in Design and Targeted Reaction of Oligonucleotide Derivatives, CRC Press, Boca Raton, Fla., pages 100 et seq., U.S. Pat. No. 4,458,066, U.S. Pat. No. 4,500,707, U.S. Pat. No. 5,153,319, U.S. Pat. No. 5,869,643, EP 0294196, and elsewhere The phosphoramidite and phosphite triester approaches are most broadly used, but other approaches include the phosphodiester approach, the phosphotriester approach and the H-phosphonate approach. The foregoing references and all other references cited in this application area incorporated herein by reference, except insofar as they may conflict with anything in the present application.

Embodiments of methods of the present invention can use the conventional sequence described above except the oxidizing step of step (c) is replaced with the sulfurization step described herein.

Sulfurization of Oligonucleotides

Most of the known sulfurization reagents, have different drawbacks in their utilization with respect to 1) ability to transfer the sulfur in excellent yields, and thus minimizing the formation of P=O units (measured by P=S/P=O ratio) 2) good solubility of the sulfurization reagent 3) stability of the solutions employed to carry the sulfurization 4) time dependency on optimum activity of the solutions (aging process) 5) short reaction times 6) no side reactions with other parts of the molecule, and finally 7) cost of the reagent and easy availability. The reaction of tri-valent phosphorus P(III) with carbonyl disulfides sulfur transfer reagents has long been known to be limited by the dielectric constant of the solvent that is utilized; this was specifically described by Vu, H. and Hirschbein, B. L. (1991) Tetrahedron Lett., 32, 3005-3008. It is this property that has made acetonitrile (dielectric constant≈37) the most obvious choice of solvents for these reactions. The reaction of carbonyl disulfide is proposed to occur by a 2-step mechanism in which the first step is an attack of the lone pair of electrons of the tri-valent phosphorus on one of the sulfur atoms of the disulfide. This produces an intermediate in which the phosphorus atom caries a positive charge, which is stabilized by the use of a high dielectric constant solvent and allow for the equilibrium to more favor this product. The second step of the reaction is the attack of the thio-acid released in the first step of this reaction, on the carbonyl groups of the positively charged phosphorus intermediate producing the desired pentavalent phosphorus P(IV) compound containing a non-bridging sulfur atom. To utilize this reaction in a lower dielectric constant solvent such as xylene, toluene (dielectric constant≈3) or 2-methyl-tetrahydrofuran (dielectric constant≈7) an acylation catalyst is utilized to speed up the second step of the reaction and possibly increase the overall yield of the reaction. It is noteworthy to point out that the acylation catalyst may also increase the efficiency of this reaction in high dielectric constant solvents like acetonitrile, dimethylsulfoxide (DMSO; dielectric constant≈42), or propylene carbonate (dielectric constant≈64).

There are essentially two types of acylation catalysts, Lewis-Acid catalysts and nucleophilic catalysts. In a first initial screen, it was found that the best effects in increasing the yield of the sulfur-transfer reaction in low dielectric constant solvents was obtained using nucleophillic catalysts such as dimethylaminopyridine (DMAP), 1,4-diazabicyclo[2.2.2] octane (DABCO), N-methylimidazole (NMI), phosphabicylooctane (PBO), 4-pyrrolodinopyridine (4-PDP), 1,5,7-Triazabicyclo[4.4.0]dec-5-ene (DEC) and the like. Of the catalysts that were tested, NMI gave the best results and offers some advantages over the other reagents. NMI is a well-known characterized reagent typically utilized in oligonucleotide synthesis for capping the un-reacted hydroxyl groups with acetic anhydride after coupling of the phosphoramidite reagent to the growing chain of the oligonucleotide. Additionally, NMI has the broadest spectrum of solubility in desirable solvents such as toluene, 2-methyl-THF, 1-methylpyrrolidinone (NMP), and acetonitrile. The addition of NMI to any of these solvents had a remarkable effect in the sulfur-transfer reaction. In the presence of low amounts of NMI such as 10% by volume or less, and in solvents with low dielectric constants, previously deemed not suited for the sulfurization reaction, the conversion of the phosphite internucleotide linkage to phosphorothioate linkages was obtained with the same or greater efficiency as compared to previously reported conditions in high dielectric constant solvents such as acetonitrile. This effect was most remarkably seen using phenyldiacetyldisulfide (PADS). A 0.2 M solution of PADS in acetonitrile gave an average of 93.4% conversion of a phosphite triester P(OR)$_3$ internucleotide bond to the corresponding phosphorothioate triester PS(OR)$_3$ when reacted for 2 minutes on solid support using a 100 fold excess of the PADS reagent as compared to the internucleotide bond. Under the same conditions, a 0.2 M solution of PADS in toluene gave only a 7.2% conversion to the phosphorothioate triester PS(OR)$_3$. The preferred conditions for using PADS described in the prior art are PADS at 0.2M concentration in a 50/50 (v/v) solution of acetonitrile and the highly toxic aromatic amine; 3-picoline. Under these conditions, a freshly prepared solution of 0.2M PADS in 50/50 (v/v) acetonitrile and 3-picoline gave 99.6% conversion to the desired phosphorothioate triester. However, if 10% in volume of NMI is added to a freshly prepared toluene solution of 0.2 M PADS, the conversion to the phosphorothioate triester drastically increases from 7.2% to 99.7%. This remarkable result was repeated with a variety of solvents and in all cases, the addition of an acylation catalyst like NMI allows for the use of low to moderate dielectric constant solvents like toluene (dielectric constant 2.4), xylene (dielectric constant 2.4), dichloromethane (dielectric constant 9), 1-methylpyrrolidinone (dielectric constant ~30), cyclopentyl methyl ether (dielectric constant 4.7), or 2-methyl tetrahydrofuran (2-Me-THF; dielectric constant 6.9), and gives comparable results to the use of high dielectric constant solvents like acetonitrile and propylene carbonate (FIG. 4). This discovery represents a significant industrial process improvement for the chemical synthesis of oligonucleotides containing sulfur substitutions on the internucleotide phosphodiester bonds.

It is important to note that even very small increases in the percentage of internucleotide bonds that are sulfurized at each step can have drastic and significant impact on the overall sulfurization of the desired oligonucleotide product. For clinical application it is desirable to maximize the overall sulfurization of the molecule (PS) and minimize the oxidation (PO). For oligonucleotides used in clinical applications, a typical sequence can have at least 20 sulfurized internucleotide bonds. The overall effective sulfurization of the molecule is calculated by taking the single step sulfurization yield and raising it to the power of the number sulfurized internucleotide bonds. As an example a 99.0% stepwise sulfurization for 20 internucleotide bonds results in an overall sulfurization efficiency of 82%; whereas, a 99.8% stepwise sulfurization for 20 internucleotide bonds results in an overall sulfurization efficiency of 96%. In this example there is a significant and important difference between an oligonucleotide that 82% sulfurized internucleotide bonds and an oligonucleotide that has 96% sulfurized internucleotide bonds; this difference can have a significant clinical impact.

Recently, further optimization of the use of PADS for oligonucleotide synthesis was described by Kortz, et. al., (2004) *Org. Proc. Res. Dev.*, 8 (6) 852-858. In this manuscript the authors, describe that the optimum conditions for sulfur transfer is a 0.2M solution of PADS in 50/50: v/v acetonitrile and 3-picoline that has been aged for at least 24 hours. The authors report that a freshly prepared solution of PADS under these conditions gives 99.5 to 99.7% conversion to the desired phosphorothioate triester. However, if the solution is prepared and let at room temperature for 24 hours or greater in other words "aged"), the aged solution gives 99.9% conversion to the desired phosphorothioate triester. The authors explain the better results by the formation of polysulfides that are more reactive than the initial disulfide.

The aging of a sulfurization reagent for 24 hours or greater to achieve optimum utility is highly undesirable, especially under GMP manufacturing conditions. The aging process is difficult to control and define and needs to be tested and defined prior to utilization. As a clear improvement over the previous protocols, the use of NMI in high dielectric constant solvents like acetonitrile or propylene carbonate provides that a freshly prepared solution PADS can achieve comparable conversion to the desired phosphorothioate triester as an aged solution (PADS in toluene or acetonitrile). A 0.2 M solution of PADS with 10% NMI (by volume) gave an average of 99.8% or greater conversion in acetonitrile, or in propylene carbonate. Remarkably, a fresh solution of PADS in 2-methyl THF with 10% NMI also gave a 99.8% conversion to the desired phosphorothioate triester and in all cases aged solutions of PADS containing 10% NMI outperform aged solutions not containing NMI.

The synthetic methods described herein may be conducted on a solid support having a surface to which chemical entities may bind. In some embodiments, multiple oligonucleotides being synthesized are attached, directly or indirectly, to the same solid support and may form part of an array. An "array" is a collection of separate molecules of known monomeric sequence each arranged in a spatially defined and a physically addressable manner, such that the location of each sequence is known. The number of molecules, or "features," that can be contained on an array will largely be determined by the surface area of the substrate, the size of a feature and the spacing between features, wherein the array surface may or may not comprise a local background region represented by non-feature area. Arrays can have densities of up to several hundred thousand or more features per $cm_2$, such as 2,500 to 200,000 features/$cm_2$. The features may or may not be covalently bonded to the substrate. An "array," or "chemical array' used interchangeably includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. An array is "addressable" when it has multiple regions of different moieties (e.g., different polynucleotide sequences) such that a region (i.e., a "feature" or "spot" or "well" of the array) at a particular predetermined location (i.e., an "address") on the array will detect a particular target or class of targets (although a feature may incidentally detect non-targets of that feature). Array features are typically, but need not be, separated by intervening spaces. An array of polynucleotides, as described herein, may include a two or three dimensional array of beads. In certain cases, the beads are linked to an oligonucleotide that has two portions, a first portion that binds to a target, and a second portion that contains a nucleotide sequence that identifies the oligonucleotide. In other cases, the bead may provide an optical address for the oligonucleotide, thereby allowing the identity of the oligonucleotide to be determined. The array may be in the form of a 3-dimensional multiwall array such as the Illumina BeadChip. One embodiment of BeadChip technology is the attachment of oligonucleotides to silica beads. The beads are then randomly deposited into wells on a substrate (for example, a glass slide). The resultant array is decoded to determine which oligonucleotide-bead combination is in which well. The arrays may be used for a number of applications, including gene expression analysis and genotyping. The address is a unique sequence to allow unambiguous identification of the oligonucleotide after it has been deposited on the array. Bead Arrays may have, for example, 1,000 to 1,000,000 or more unique oligonucleotides. Each oligonucleotide may be synthesized in a large batch using standard technologies. The oligonucleotides may then be attached to the surface of a silica bead, for example a 1-5-micron bead. Each bead may have only one type of oligonucleotide attached to it, but have hundreds of thousands of copies of the oligonucleotide. Standard lithographic techniques may be used to create a honeycomb pattern of wells on the surface, for example a glass slide. Each well may hold a bead. The beads for a given array may be mixed in equal amounts and deposited on the slide surface, to occupy the wells in a random distribution. Each bead may be represented by, for example, about 20 instances within the array. The identity of each bead may be determined by decoding using the address sequence. A unique array layout file may then associated with each array and used to decode the data during scanning of the array.

In some embodiments, oligonucleotides being synthesized may be attached to a solid support (for example: beads, membrane, 96-well plate, array substrate, filter paper and the like) directly or indirectly. Suitable solid supports may have a variety of forms and compositions and derive from naturally occurring materials, naturally occurring materials that have been synthetically modified, or synthetic materials. Examples of suitable support materials include, but are not limited to, control pore glass (CPG), silicas, teflon, glasses, polysaccharides such as cellulose, nitrocellulose, agarose (e.g., Sepharose (from Pharmacia) and dextran (e.g., Sephadex and Sephacyl, also from Pharmacia), polyacrylamides, polystyrenes, polyvinyl alcohols, copolymers of hydroxyethyl methacrylate and methyl methacrylate, and the like. The initial monomer of the oligonucleotide to be synthesized on the solid support, e.g. CPG, bead, or array substrate surface, can be bound to a linking moiety (for example, a succinyl linker, or a hydroquinone —O,O'-diacidic acid called a "Q-linker", an oxalyl linker, and the like) which is in turn bound to a surface hydrophilic group, e.g., a surface amine or a hydroxyl present on a silica substrate. In some embodiments, a universal linker is used (for example, Unylinker which is a succinyl derivative of 8,9-Dihydroxy-4-phenyl-10-oxa-4-aza-tricyclo[5.2.1.02,6]decane-3,5-dione, or other Glenn Research universal supports). In some embodiments, an initial nucleotide monomer is reacted directly with a reactive site, e.g. a surface amine or hydroxyl present on the substrate. In some embodiments wherein the initial nucleotide monomer is reacted directly with the reactive sites on the surface, the oligonucleotide remains covalently attached to the surface post oligonucleotide synthesis and deprotection, after all of the protecting groups are removed. In some embodiments, a nucleotide monomer is reacted with a non-nucleoside hydroxyl or amine that is not part of a nucleoside or nucleotide. Alternatively, in some embodiments, an oligonucleotide can be synthesized first and then attached to a solid substrate post-synthesis by any suitable method. Thus, particular embodiments can be used to prepare an array of oligonucleotides wherein the oligonucleotides are either synthesized on the array, or attached to the array substrate post-synthesis.

EXAMPLES

Synthesis of TT Dimers (General Procedure)

All DNA phosphorothioate dimers syntheses were performed on 1 mmole scale using thymidine attached to controlled pore glass beads (CPG) by a succinic acid linker or a hydroquinone linker (Q-linker), both of which are commercially available columns from Glen Research, Sterling Va. For the purpose of the experiments, the standard 1 mmole cyanoethyl cycle was modified by replacing capping step with thiolation on an Applied Biosystems model 394 DNA/RNA synthesizer, Foster City, Calif. After standard 25 sec coupling, CPG was washed with MeCN and dried with argon. Thiolating solution (placed in bottle 11) was then delivered to the column for 15 sec, and let sit for 2 minutes. After that time, CPG was washed with DCM, followed by MeCN, and the cycle continued with standard $I_2$ oxidation (to ensure complete conversions all P-III phosphites into stable P-V triesters—in case not all the linkages were oxidized with sulfur) and final detritylation.

Cleavage from the support and deprotection were done in gas ammonia (70 psi) at RT for 2.5 hours. After venting the ammonia gas, crude products were dissolved in water (1 mL), filtered and analyzed by RP-HPLC(ODS-Hypersil column, 5 mm 4.0×250 mm, 0.1M TEAA buffer with MeCN gradient (0-20% in 40 minutes). The ratio of phosphodiester to phosphorothioatediester was determined by peak integration (FIG. 1) on an Agilent Technologies, model 1200 High Performance Liquid Chromatography (HPLC) System, Santa Clara, Calif.

I. PADS Thiolation Efficiency in Different Solvents without the Use of N-Methyl Imidazole A series of experiments were carried out to evaluate the efficiency of PADS thiolation of a TT dimer in different solvent systems and without the use of N-methyl imidazole as an acylation catalyst.

The efficiency of thiolation was calculated as explained above by determining the ratio of phosphodiester amount to phosphorothioatediester amount extrapolated by peak area integration of the phosphodiester and phosphorothioate species from the HPLC chromatogram.

The results are summarized in the FIG. 5.

II. Titration of NMI in 0.2M Pads Solutions.

A two set of series of experiments were carried out to determine the optimal amount of acylation catalysts (NMI) needed to give the best thiolation results with PADS at 0.2M in different solvent systems. The first set was performed with freshly made PADS solutions and the second set was performed with 24 hrs aged solutions. The efficiency of sulfurization of the phosphite intermediate to a phosphorothioate linkage of a TT-dimer was calculated as described previously, by determining the ratio of phosphate diester to phosphorothioate diester from the HPLC chromatogram. The results are summarized in FIGS. 6a-8b).

III. Synthesis of Test Phosphorothioate 13-mer (all DNA) with Various Pads Formulations.

Instrumentation: GE Akta Oligopilot 100

Synthesis Details: 5' gCA TTg gTA TTC T 3' synthesized at 490 μMol synthesis scale on GE PS200 solid support loaded at 204 μMol/g with 2' deoxy Thymidine Standard oligonucleotide synthesis cycle:

Detritylation

3% Dichloroacetic Acid in Dichloromethane

Coupling 0.2M phosphoramidites in acetonitrile 0.5M EthylthioTetrazole in acetonitrile 2 eq. of monomer (relative to synthesis scale)

3.7:1 ethylthiotetrazole (ETT:monomer molar ratio)

Recycled for 7 minutes

Oxidation/Thiolation 3.92 eq. of thiolation reagent (relative to synthesis scale)

~12 minutes total contact time

Thiolation Solutions Utilized 0.2M PADS in Propylene Carbonate/10% N-Methyl Imidazole, freshly prepared 0.2M PADS in Toluene/10% N-Methyl Imidazole, freshly prepared 0.2M PADS in Toluene/10% N-Methyl Imidazole, ~24 hours aged 0.2M PADS in Acetonitrile/3-Picoline (1:1), freshly prepared 0.2M PADS in Acetonitrile/3-Picoline (1:1), ~24 hours aged Capping 0.5 column volume each reagent, delivered simultaneously 20% n-Methyl Imidazole in Acetonitrile 5:3:2 Acetonitrile:2,6-Lutidine:Acetic Anhydride Cleavage and Deprotection Solid support samples of ~100 mg were deprotected in 1 ml aqueous Methyl Amine for 1 hour at 40° C., cooled, filtered & diluted with deionized water.

Analysis

Analysis performed on Agilent 6330 Ion Trap LC/MS

Tabulated mass-spec data from Thiolation synthesis experiments

| PADS Solutions | P=S % | P=O % | Calculated stepwise efficiency (%) |
|---|---|---|---|
| 0.2M PADS in Propylene Carbonate/ N-Methyl Imidazole, 90/10, v/v, freshly prepared | 94.5 | 5.5 | 99.53 |
| 0.2M PADS in Toluene/ N-Methyl Imidazole, 90/10, v/v, freshly prepared | 96.4 | 3.6 | 99.69 |
| 0.2M PADS in Toluene/ N-Methyl Imidazole, 90/10, v/v, ~24 hours aged | 97.4 | 2.6 | 99.78 |
| 0.2M PADS in Acetonitrile/ 3-Picoline (1:1), freshly prepared | 94.5 | 5.5 | 99.53 |
| 0.2M PADS in Acetonitrile/ 3-Picoline (1:1), ~24 hrs | 97.4 | 2.6 | 99.78 |

Efficiency Calculation

There are 12 thiolation reactions in the test molecule (13 nucleosides), so the stepwise efficiency can be calculated by the following formula.

$$\%P = \sqrt[12]{S/100}$$

Example:

$$\sqrt[12]{97.4/100} = 0.9978 = 99.78\%$$

Ion Trap LC/MS Data (FIGS. 3a and 3b) of a 13-Mer Phosphorothioate DNA Sulfurized With 0.2M Pads in Propylene Carbonate/NMI Fresh Solution.

LC Buffer: 5 mM NH4OAc/MeOH.

From the mass spectrometry chromatogram and the quantitative data associated with it, it is possible to determine the total amount of P=O (expressed in %) in the sample. From these data, it is possible thus to determine the total amount of P=S in the same sample and to calculate the average stepwise sulfurization efficiency using the formula as shown previously.

For example, in the m/z data obtained from the mass spectrum of phosphorothioate 13-mer DNA thiolated with 0.2 M PADS in propylene carbonate/NMI:90/10 (v/v)) fresh solution (chromatogram shown in FIG. 3b), the total P=O amount is given as 5.5%, thus total P=S is calculated as 94.5%, and the average stepwise thiolation efficiency is calculated as $0.945^{(1/12)} = 0.9953$ or 99.53%.

ABBREVIATIONS

In this application, the following abbreviations have the following meanings. Abbreviations not defined have their generally accepted meanings.
° C.=degree Celsius
hr=hour
min=minute
sec=second
μM=micromolar
mM=millimolar
M=molar
ml=milliliter
μl=microliter
mg=milligram
μg=microgram
v/v=volume/volume
DMAP=4,4'-dimithylaminopyridine
DMT=4,4'-dimethoxytrityl
DCM=Dichloromethane
MeCN=Acetonitrile
2-Me-THF=2-Methyl-tetrahyfdrofuran
NMI=N-methyl Imidazole
Py=Pyridine
Pic=3-Picoline
TEA=triethylamine
TEAA=triethylammonium acetate
TEAB=triethylammonium bicarbonate
TEMED=N,N,N',N'-tetramethylethylenediamine
TBAF=tetrabutylammonium fluoride
TBDMS=tert-butyl-dimethylsilyl
RP-HPLC=Reverse Phase High Performance Liquid Chromatography
RT=Room Temperature One or more embodiments of the invention may provide for one or more, or other, useful aspects such as now discussed. However, these are not limiting of the invention nor any particular embodiment. Chemical synthesis of biologically important alkyl phosphite products and the chemical entities useful in such synthesis, and oxidative addition of sulfur to such phosphites intermediates. The formation of P=S linkages in biologically important compounds may be allowed, without the need for solvents with high dielectric constants. Sulfur addition according to one or more embodiments may take place with high yields, in either the current industrially preferred large-scale solvents or solvents that are derived from renewable resources. The renewable solvents have a significantly lower carbon footprint than the current industrial petrochemical based solvents which may be prone to production shortages and price volatility. The thiolation reaction may also be significantly less expensive, and may give equally high or higher efficiency of sulfur transfer than methods that use industrially non-preferred solvents.

Although the present invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of embodiments of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

The invention claimed is:

1. A method of sulfurizing at least one phosphite or thiophosphite linkage in an oligonucleotide, said method comprising:
   providing a phosphite or thiophosphite intermediate; and
   contacting said phosphite or thiophosphite intermediate with a composition comprising an acetyl disulfide, a solvent, and N-alkyl imidazole, for a time sufficient to convert said phosphite or thiophosphite intermediate to said phosphorothioate or phosphorodithioate
   wherein said solvent is a low dielectric constant solvent.

2. A method according to claim 1 wherein said N-alkyl imidazole is N-methyl imidazole.

3. The method of claim 1 wherein said N-alkyl imidazole is at least 1% in volume (v/v) in said solvent.

4. The method of claim 1 wherein said N-alkyl imidazole is at least 5% in volume (v/v) in said solvent.

5. The method of claim 1 wherein said acetyl disulfide is at least at 0.1M concentration in said solvent.

6. The method of claim 2 wherein said acetyl disulfide is at a concentration of at least 0.1 M and said N-methyl imidazole is at least 5% in volume (v/v) in said solvent.

7. The method of claim 1 wherein said oligonucleotide comprises one or more ribonucleotides.

8. The method of claim 1 wherein said oligonucleotide comprises at least one nucleotide analogue.

9. A method of sulfurizing at least one phosphite or thiophosphite linkage in an oligonucleotide, said method comprising:
   providing a phosphite or thiophosphite intermediate
   contacting said phosphite or thiophosphite intermediate with a composition comprising phenylacetyl disulfide, a solvent, and N-methyl imidazole for a time sufficient to convert said phosphite or thiophosphite intermediate to said phosphorothioate or phosphorodithioate
   wherein said solvent is a low dielectric constant solvent.

10. The method of claim 9 wherein said solvent comprises toluene, xylene, 2-methyl THF or cyclopentyl methyl ether.

11. The method of claim 10 wherein said solvent is toluene.

12. The method of claim 10 wherein said solvent is 2-methyl THF.

13. The method of claim 9 wherein said solvent is toluene, and wherein said phenylacetyl disulfide is at a concentration of at least 0.1 M and said N-methyl imidazole is at least 5% in toluene (v/v).

14. The method of claim 9 wherein said solvent is toluene, said phenylacetyl disulfide is at a concentration of 0.2 M and said N-methyl imidazole is between 10% to 20% in toluene (v/v).

15. The method of claim 9 wherein said solvent is 2-methylTHF, and wherein said phenylacetyl disulfide is in a concentration of at least 0.1 M and said N-methyl imidazole is at least 5% in volume in 2-methyl THF (v/v).

16. The method of claim 9 wherein said solvent is 2-methyl THF, said phenylacetyl disulfide is in a concentration of 0.2 M and said N-methyl imidazole is 5% to 20% in volume in 2-methyl THF (v/v).

17. A method of sulfurizing at least one phosphite or thiophosphite linkage in an oligonucleotide, said method comprising:
   providing a phosphite or a thiophosphite bound to a solid support,
   contacting said phosphite or thiophosphite with a composition comprising N-alkyl imidazole, an acetyl disulfide, and a solvent for a time sufficient to convert said phosphite or thiophosphite to said phosphorothioate or phosphorodithioate linkage
   wherein said solvent is a low dielectric constant solvent.

18. The method of claim 17 wherein said solid support is controlled pore glass or polystyrene.

19. The method of claim 18 wherein said solid support is an array or beads.

20. The method of claim 17 wherein said solvent is selected from toluene, xylene, 2-methyl THF and cyclopentyl methyl ether.

21. The method of claim 20 wherein N-alkyl imidazole is at least at 5% in volume and the acetyl disulfide is at least at 0.1 M concentration in said solvent.

* * * * *

UNITED STATES PATENT AND TRADEMARK OFFICE
CERTIFICATE OF CORRECTION

PATENT NO. : 8,309,710 B2
APPLICATION NO. : 12/494118
DATED : November 13, 2012
INVENTOR(S) : Agnieszka B. Sierzchala et al.

Page 1 of 1

It is certified that error appears in the above-identified patent and that said Letters Patent is hereby corrected as shown below:

On the face page, in field (56), under "Other Publications", in column 2, line 16, delete "Phosphorothloate" and insert -- Phosphorothioate --, therefor.

On the face page, in field (56), under "Other Publications", in column 2, line 36, delete "chemistsa re" and insert -- chemists are --, therefor.

On the face page, in field (56), under "Other Publications", in column 2, line 39, delete "Oligonucleoitide" and insert -- Oligonucleotide --, therefor.

On the face page, in field (56), under "Other Publications", in column 2, line 44, delete "Chmistry" and insert -- Chemistry --, therefor.

On the face page, in field (56), under "Other Publications", in column 2, line 56, delete "Phosphorotioate" and insert -- Phosphorothioate --, therefor.

In column 18, lines 13-14, in Claim 15, delete "methylTHF" and insert -- methyl THF --, therefor.

Signed and Sealed this
Fifteenth Day of January, 2013

David J. Kappos
*Director of the United States Patent and Trademark Office*